US010143427B2

(12) United States Patent
Smith et al.

(10) Patent No.: US 10,143,427 B2
(45) Date of Patent: Dec. 4, 2018

(54) SEGMENTED DIRECT DRIVE MOTOR FOR USE IN A COMPUTED TOMOGRAPHY SYSTEM

(71) Applicant: General Electric Company, Schenectady, NY (US)

(72) Inventors: Chad Allan Smith, Waukesha, WI (US); James Charles Bartelsen, Nashotah, WI (US)

(*) Notice: Subject to any disclaimer, the term of this patent is extended or adjusted under 35 U.S.C. 154(b) by 290 days.

(21) Appl. No.: 15/008,255

(22) Filed: Jan. 27, 2016

(65) Prior Publication Data

US 2017/0214279 A1 Jul. 27, 2017

(51) Int. Cl.

| | |
|---|---|
| *A61B 6/03* | (2006.01) |
| *H02K 11/20* | (2016.01) |
| *A61B 6/00* | (2006.01) |
| *H02K 1/12* | (2006.01) |
| *H02K 7/08* | (2006.01) |
| *H02K 11/00* | (2016.01) |
| *H02K 15/02* | (2006.01) |
| *H02K 41/00* | (2006.01) |

(52) U.S. Cl.
CPC .............. *A61B 6/035* (2013.01); *A61B 6/032* (2013.01); *A61B 6/54* (2013.01); *H02K 1/12* (2013.01); *H02K 7/08* (2013.01); *H02K 11/0094* (2013.01); *H02K 11/20* (2016.01); *H02K 15/02* (2013.01); *H02K 41/00* (2013.01); *F16C 2300/14* (2013.01)

(58) Field of Classification Search
CPC .................................. A61B 6/032; A61B 6/035
USPC ......................................... 378/15, 196, 197
See application file for complete search history.

(56) References Cited

U.S. PATENT DOCUMENTS

| | | | | |
|---|---|---|---|---|
| 4,276,490 | A | | 6/1981 | Saldinger |
| 4,723,259 | A | * | 2/1988 | Amor ..................... A61B 6/032 378/10 |
| 4,798,540 | A | * | 1/1989 | Bernardi ............. A61B 6/4447 378/15 |
| 4,799,245 | A | * | 1/1989 | Bernardi ............. A61B 6/4447 378/15 |
| 5,740,222 | A | * | 4/1998 | Fujita ..................... A61B 6/032 378/4 |
| 5,869,915 | A | * | 2/1999 | Blake .................. H02K 17/165 310/166 |
| 6,321,439 | B1 | | 11/2001 | Berrong et al. |
| 6,412,345 | B1 | * | 7/2002 | Murray ................. A61B 6/035 73/462 |
| 6,429,554 | B1 | | 8/2002 | Albrich et al. |
| 6,492,756 | B1 | | 12/2002 | Maslov et al. |

(Continued)

FOREIGN PATENT DOCUMENTS

DE 10304030 A1 9/2004

OTHER PUBLICATIONS

International Search Report and Written Opinion for corresponding PCT application No. PCT/US2017/014828 dated Apr. 12, 2017; 12 pages.

*Primary Examiner* — Allen C. Ho (57) ABSTRACT

The present approach includes, in one implementation, a direct drive motor for use in a CT gantry and having a segmented motor stator assembly. The stator segments are connected in series. The stator segments are not independently operable and are instead connected in series to, and operated by, a single frequency controller.

19 Claims, 5 Drawing Sheets

(56) References Cited

U.S. PATENT DOCUMENTS

| | | | |
|---|---|---|---|
| 6,553,091 B2 * | 4/2003 | Takanashi | A61B 6/035 378/15 |
| 6,590,953 B2 * | 7/2003 | Suzuki | A61B 6/035 310/211 |
| 6,940,941 B2 * | 9/2005 | Gregerson | A61B 6/032 250/363.05 |
| 7,108,421 B2 * | 9/2006 | Gregerson | A61B 6/032 378/197 |
| 7,183,689 B2 | 2/2007 | Schmidt et al. | |
| 7,202,580 B2 * | 4/2007 | Yokoyama | A61B 6/56 310/68 B |
| 7,291,840 B2 * | 11/2007 | Fritzler | G01T 1/1615 250/363.03 |
| 7,477,721 B2 * | 1/2009 | Chappo | A61B 6/032 378/13 |
| 7,514,885 B2 * | 4/2009 | Hausner | A61B 6/035 212/284 |
| 7,593,502 B2 * | 9/2009 | Katcha | A61B 6/032 378/101 |
| 7,760,850 B2 * | 7/2010 | Kasuya | A61B 6/035 378/15 |
| 8,054,943 B2 * | 11/2011 | Danyluk | H01J 35/101 378/125 |
| 8,170,175 B2 * | 5/2012 | Kasuya | A61B 6/56 378/15 |
| 8,237,123 B2 * | 8/2012 | Yakubovsky | A61B 6/032 250/363.02 |
| 8,270,563 B2 * | 9/2012 | Harris | A61B 6/035 378/15 |
| 8,299,670 B2 | 10/2012 | Krumme | |
| 8,447,560 B2 * | 5/2013 | Vaisburd | G01C 9/00 702/151 |
| 9,084,335 B2 * | 7/2015 | Mekonnen | H05G 1/10 |
| 9,173,618 B2 * | 11/2015 | Hermony | A61B 6/032 |
| 9,254,108 B2 * | 2/2016 | Maki | A61B 6/4435 |
| 9,314,220 B2 * | 4/2016 | Luhta | A61B 6/56 |
| 9,314,221 B2 * | 4/2016 | Katcha | A61B 6/56 |
| 9,526,461 B2 * | 12/2016 | Gregerson | A61B 6/032 |
| 9,538,963 B2 * | 1/2017 | Smithanik | A61B 6/035 |
| 9,668,330 B2 * | 5/2017 | Matsuzawa | A61B 6/035 |
| 9,974,496 B2 * | 5/2018 | Liu | A61B 6/0457 |
| 9,974,980 B2 * | 5/2018 | Liu | A61N 5/1081 |
| 2001/0055362 A1 | 12/2001 | Takanashi et al. | |
| 2002/0031201 A1 | 3/2002 | Sukuki et al. | |
| 2012/0032084 A1 | 2/2012 | Sapp et al. | |

\* cited by examiner

SEGMENTED DIRECT DRIVE MOTOR FOR USE IN A COMPUTED TOMOGRAPHY SYSTEM

BACKGROUND

The subject matter disclosed herein relates to direct drive motors for use in a non-invasive, non-destructive imaging system. By way of example, the present discussion relates the use of certain segmented direct drive motors in the context of a computed tomography imaging system.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation spans a subject of interest, such as a human patient, and a portion of the radiation impacts a detector where the image data is collected. In digital X-ray systems a photo detector produces signals representative of the amount or intensity of radiation impacting discrete pixel regions of a detector surface. The signals may then be processed to generate an image that may be displayed for review. In CT systems a detector array, including a series of detector elements, produces similar signals through various positions as a gantry is displaced around a patient.

In particular, in CT imaging systems the gantry is conventionally used to spin the X-ray source and detector components around the imaging volume in which the patient is positioned during a scan. Some CT systems may employ a direct drive motors to spin the CT gantry, to which the X-ray tube and the detector are affixed, around the patient. As used herein, a direct drive motor, in contrast to a belt drive or geared drive, applies power from a motor to a driven load (here a CT gantry) without any reductions in power, such as may be associated with a gearbox. In conventional direct drive contexts, the direct drive motor assembly is typically provided as a full 360 degree ring structure.

Such a construction provides a variety of challenges to fabrication and use. For example, traditionally CT scanners have needed high torque motors to accelerate and decelerate the gantry quickly in order to minimize the amount of time that the components on the rotating gantry spend under the high gravitational (i.e., high-G) forces. Such high torque motors have conventionally required a large number of windings, which equates to greater complexity, greater weight, and greater expense of the motor. Similarly, the expense and complexity of these motors has limited the availability of direct drive motor technology, which is generally quieter, to higher end systems.

In addition, direct drive designs utilizing a full ring structure also present certain challenges in terms of maintenance and servicing. In particular, while direct drive motors can provide benefits to a CT such as quiet and smooth operation, they cannot be replaced in the hospital like a belt driven CT gantry can (which utilize a smaller motor plus a belt driven system). Direct drive motor armatures are typically too large and heavy to replace in a hospital room.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a motor assembly for directly driving a gantry of a computed tomography (CT) imaging system is provided. In accordance with this embodiment, the motor assembly comprises: a motor stator comprising two or more separate stators segments electrically connected in series to form a partial ring, and a motor rotor configured as a ring and positioned within the partial ring of the motor stator.

In a further embodiment, a method of assembling a motor assembly of a direct drive for rotating a computed tomography (CT) gantry is provided. In accordance with this embodiment, a motor rotor is affixed to a bearing rotor rotationally coupled to a bearing stator. A plurality of stator segments are affixed to the bearing stator so as to form a partial ring along the bearing stator. The plurality of stator segments are electrically connected in series. A first stator segment is connected to a frequency controller.

In an additional embodiment, a computed tomography (CT) system is provided. In accordance with this embodiment, the CT system includes: a frequency controller, a motor assembly, and a bearing assembly connected to the motor assembly. The motor assembly includes: a motor stator formed as a partial ring, wherein the motor stator comprises a plurality of separate stator segments electrically connected in series, wherein a first stator segment is electrically connected to the frequency controller; and a motor rotor positioned within the motor stator and configured to rotate within the motor stator when the frequency controller applies a current to windings of each stator segment. The bearing assembly includes: a bearing rotor affixed to the motor rotor on a first rotor surface and to a CT rotor assembly on a second rotor surface; a bearing stator affixed to the motor stator on a first stator surface and to a stationary frame on a second stator surface; and a plurality of bearings between the bearing rotor and bearing stator configured to allow rotation of the bearing rotor within the bearing stator when driven by the motor assembly.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of passengers, visitors, packages, boxes, luggage, and so forth (i.e., security or screening applications). In general, the present approaches may be desirable in any imaging or screening context in which material decomposition is desirable.

Traditional direct drive motors used in computed tomography (CT) gantries (such as to spin the X-ray source and detector components about the gantry bore) are conventionally a full 360 degree ring. As discussed herein, in accordance with the present approach, a segmented brushless DC motor is instead utilized for a CT imaging system where the full ring has instead been reduced to two or more (e.g., three, four, five, six, and so forth) segments. In one implementation the segments are all powered by a single frequency controller (i.e., servo drive). As CT gantries are typically built for one set of specification and are not scalable, independent motor segments, which can be added or removed, are not needed and may be excluded. Instead, motor segments may be employed that are dependent on one another to operate in order to create a design where by the segments are closely connected to each other. This provides certain benefits, such as keeping cable lengths short for reduced radiated electrical emissions, which that may not be attainable in other contexts (e.g., industrial contexts where multiple sets of specification and/or scalability) where independent motor segments are needed and longer cable lengths are not an issue.

Figure 1:
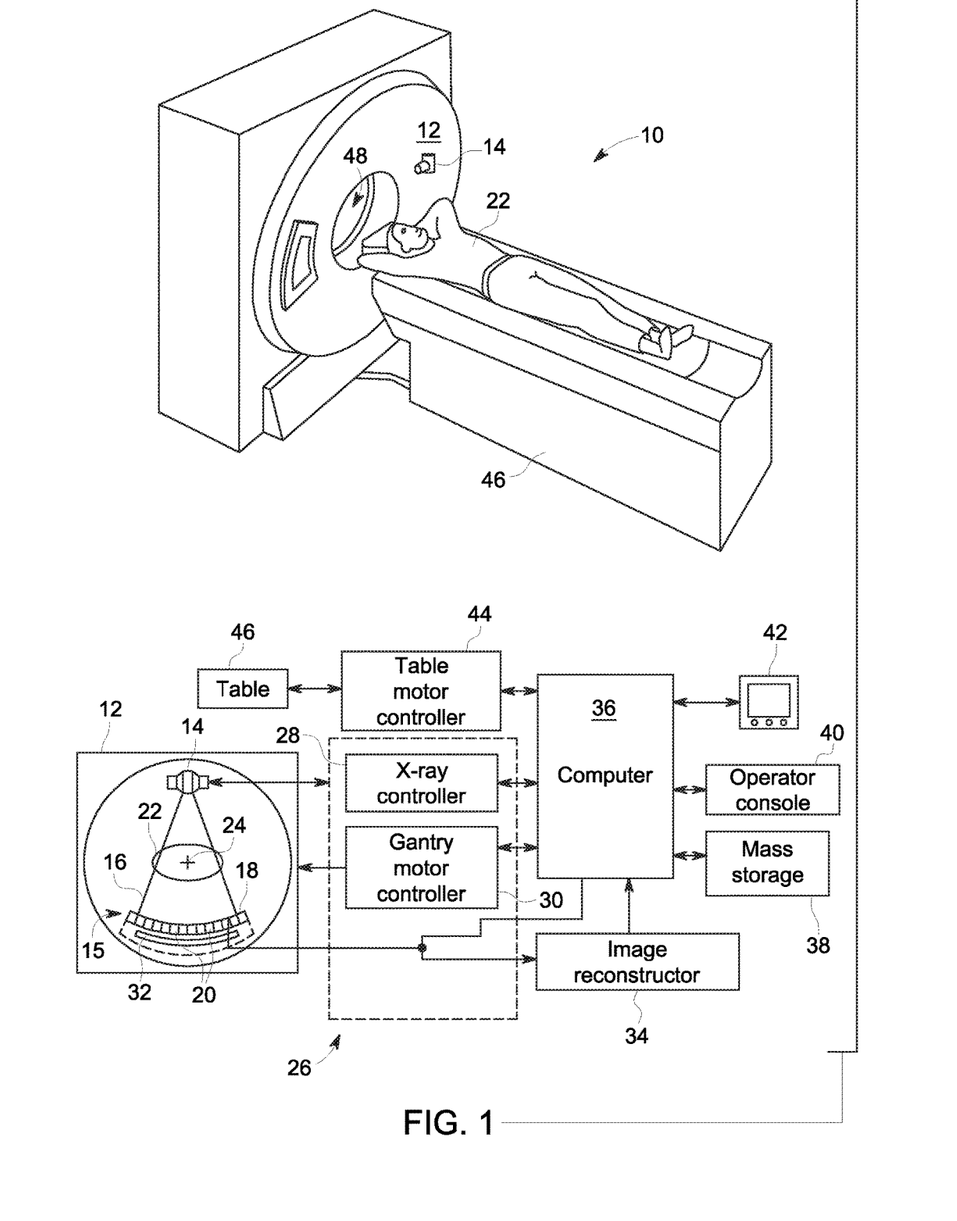
FIG. 1 is a combined pictorial view and block diagram of a computed tomography (CT) imaging system illustrating an embodiment of the present disclosure.

With the preceding in mind and referring to FIG. 1, a computed tomography (CT) imaging system 10 is shown as including a gantry 12 used to rotate scanner components around an imaging bore. Gantry 12 has an X-ray source 14 that projects a beam of X-rays 16 toward a detector assembly 15 on the opposite side of the gantry 12. The detector assembly 15 includes a collimator assembly 18, a plurality of detector modules 20, and data acquisition systems (DAS) 32. The plurality of detector modules 20 detect the projected X-rays that pass through a medical patient 22, and DAS 32 converts the data to digital signals for subsequent processing. Each detector module 20 in a conventional system produces an analog electrical signal that represents the intensity of an impinging X-ray beam and hence the attenuated beam as it passes through the patient 22. During a scan to acquire X-ray projection data, gantry 12 and the components mounted thereon rotate about a center of rotation 24.

Rotation of gantry 12 and the operation of X-ray source 14 are governed by a control mechanism 26 of CT system 10. Control mechanism 26 includes an X-ray controller 28 that provides power and timing signals to an X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 to position patient 22 and gantry 12. Particularly, table 46 moves portions of patient 22 through a gantry opening 48.

With respect to the challenges presented by the use of conventional full-ring direct drive motor designs and the benefits of the present approach, the following comments are provided by way of context to highlight benefits of the present approach.

By way of example, the present approaches provide for both lower cost and reduced torque. In conventional contexts, CT scanners have typically employed high torque motors to accelerate and decelerate the gantry quickly in order to minimize the amount of time that the components on the rotating gantry spend under the high gravitational (high G) forces. These high G-forces can degrade the life of rotating CT components such as the X-ray tube. However, advances in CT component technology have greatly extended the life of rotating components under high G-loads and therefore the need for a high torque direct drive has been reduced. The present design, therefore, allows for the use of a lower torque motor that is still capable of driving the gantry components in a manner compatible with a CT examination in terms of both rotational speed, as well as acceleration and deceleration of the gantry.

In a complementary context, the latest generation of CT scanners have larger and/or more X-ray tubes, larger and/or more detectors, and generally are heavier to support the higher rotation speeds needed to attain good temporal resolution. By way of example, conventional high-end CT gantries are in the 5,000-6,000 pound range while the elevators in many hospitals, needed to install the systems on upper floors, can typically only handle weights up to 4,500 pounds. Use of a segmented motor topology, as discussed herein, is one way that may be employed to reduce the overall scanner weight as there is correspondingly less copper employed in the winding/lamination stack. In particular, the present designs incorporate a CT segmented brushless direct drive DC motor that reduces the amount of armature winding around the magnet rotor by using segments instead of a full ring. The segments do not cover the full circumference of the motor/magnet ring and therefore result in a total motor design that has less mass.

In addition there is a need to reduce the cost of the direct drive motor technology, which is inherently very quiet (which is on benefit to the patient), so that the technology is more widely available. The present approach using a segmented brushless direct drive DC motor helps address these challenges by reducing the cost of the direct drive motor by using less windings (i.e., by employing ring segments rather than a full ring), which in turn reduces the overall cost to manufacture the motor, as segments are easier to manufacture than a full ring motor. Since these segments are smaller than a full ring, they will be easier to wind and will take less time to fabricate. Since high torque is not needed (as noted above), the segmented topology enables a lower cost and lower torque motor to be built for the CT gantry application. Thus, the designs discussed herein allow for the construction of less expensive, lighter drive systems that provide a degree of torque that is sufficient for current CT scanner requirements.

In addition, the present approach can allow for improved and/or easier servicing of the CT imaging system. In particular, CT gantries are designed so that parts can be easily and quickly replaced in the hospital in order to ensure the system is available for patient who needs it. While direct drive motors provide benefits to a CT system with respect to quiet and smooth operation, they cannot be replaced in the hospital the way a belt driven CT gantry (which employs a smaller motor plus a belt) can. In particular, direct drive motor armatures for a full ring structure are typically too large and heavy to replace in a hospital room. However, in accordance with the present approach, smaller motor segments are provided in the design that could be individually removed and replaced in the hospital. Conversely, a failure in a full ring direct drive motor requires replacing the full CT gantry, which can take the imaging system out of patient use for several days.

Lastly, in terms of the challenges and benefits posed by the present segmented direct drive motor approach discussed herein, traditional segmented motors for industrial applications are typically designed to have independently controlled segments connected to the frequency converter. This topology allows them to be scalable. It also allows the system to run at reduced performance with a segment that fails or is otherwise unavailable. However, a configuration of independent segments requires cables connecting each segment to the servo drive. This can result in long cables running to the servo drive that can emit EMC (electrical radiated emission) noise.

In a medical application, a CT gantry should have very low radiation emissions to avoid introducing unnecessary electronic noise into the reconstructed image and/or into surrounding patient electronics (e.g., patient monitors or therapeutic devices, pacemakers, network infrastructure, and so forth). Since a CT direct drive motor does not need to be scalable (i.e., it is designed for one system), cannot operate at reduced performance, and requires very low electrical radiated emissions, the present approach employs segments that are connected to one another in series configuration originating at the servo drive, with end termination, so that the wiring is short between segments and so that the distance from the servo drive to the first segment is short. Having short cables, that are fully shielded, aids in reducing the electrical radiation emissions from the motor while operating. As noted above, in such implementations, the segments are not independently operable due to being connected in series. As a result, in such a configuration segments cannot operate independently in the event of failure of one of the segments. Further, in such a configuration only a single frequency converter (i.e., servo drive) is employed which drives all connected segments.

Figure 2:
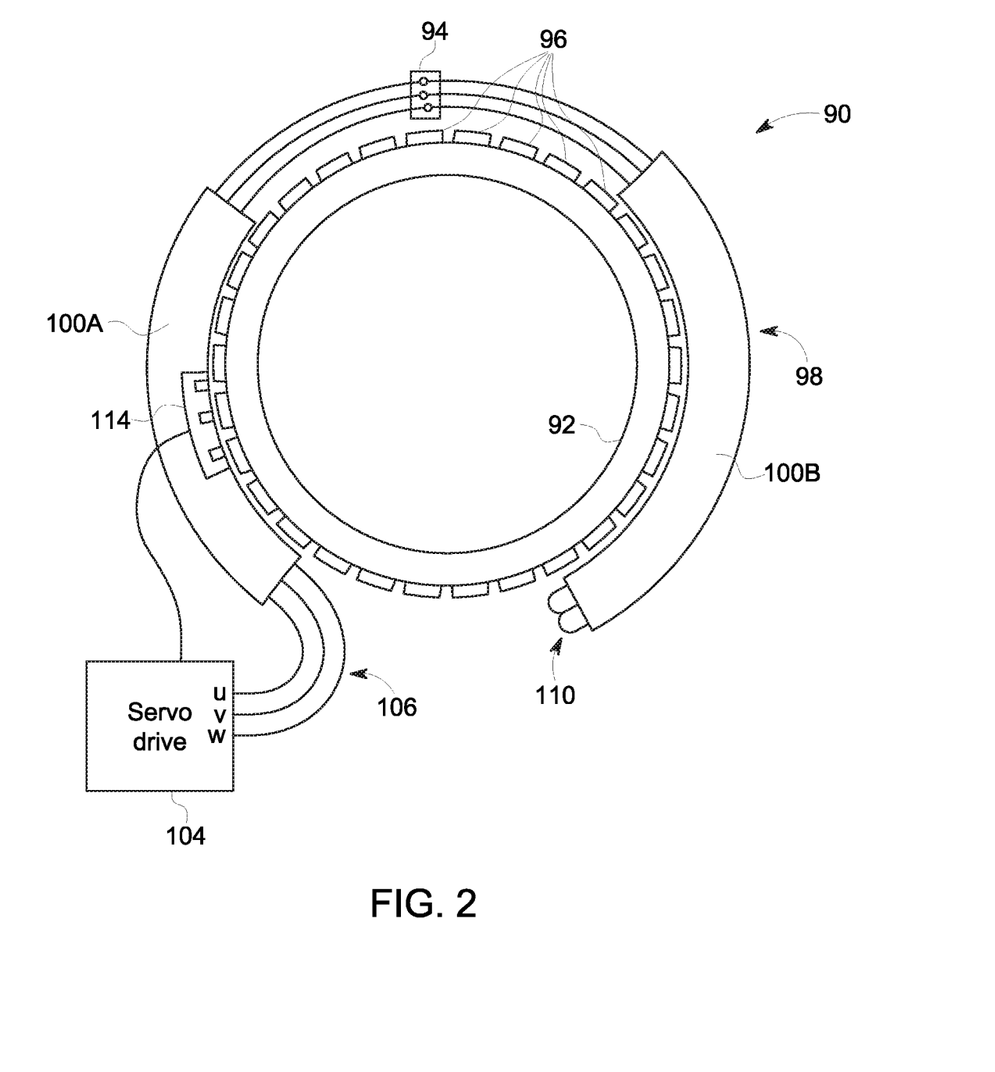
FIG. 2 depicts an assembly of a rotor and segmented stator, in accordance with aspects of the present disclosure.

With the preceding in mind, and turning to the figures, FIG. 2 depicts a segmented direct drive motor 90 for use in a gantry 12 of a CT imaging system 10. In the depicted example, the direct drive motor 90 includes a motor rotor 92 (e.g., a magnet ring) having a full ring of permanent magnets 96. The depicted direct drive motor 90 also includes a motor stator 98 formed as two (or more) stator segments (i.e., segmented armature windings) 100 (here shown as a first segment 100A and second segment 100B). The motor rotor 92 rotates with respect to (and within) the fixed or otherwise stationary stator segments 100. A terminal block 94 or other connector arrangement (e.g., two complementary high-voltage connectors) is provided between the segments 100A and 100B to electrically connect the segments. In certain implementations, more than two segments 100 may be used to form the stator 98, such as additional segments 100 provided between the depicted segments 100A and 100B. In such implementations, additional terminal blocks 94 or other connectors are also provided to electrically connect each segment 100 to an adjacent segment 100 if one is present on a respective side.

As shown, the stator segments 100 are connected in series with one another. As a result, the stator segments 100 are not independently operable, but instead are operated as a single unit. Thus, if one segment 100 fails, none of the segments 100 can be operated. Further, since the segments 100 are not independently operable, only a single frequency controller 104 (i.e., servo drive) is used to operate the motor drive. Conversely, in other implementations the stator segments may be configured to be independently operable, but the longer cables needed to connect each segment independently back to a central or main frequency controller would result in electrical radiated emissions, which are detrimental.

A frequency controller (i.e., servo drive) 104 is provided and, as shown in this example, is connected to stator segment 100A. In the depicted implementation, a single frequency controller 104 is provided and only one segment 100 is directly connected (by motor cable or conductors 106) to the frequency controller 104. That is, in accordance with the present approach, the second segment 100B does not have to be directly connected to the frequency controller 104, such as by a separate cable 106.

While the second segment 100B is not connected by a cable 106 to the frequency controller, the second segment 100B does include the motor termination connections 110. Consequently, first segment 100A, despite being connected to the frequency controller 104, is not independent since first segment 100A can only operate when plugged into (i.e., conductively connected to) second segment 100B, which is connected to the end termination structures. Similarly, second segment 100B is not independent since second segment 100B is not connected to the frequency controller 104 and does not include a feedback sensor assembly 114 (as discussed below). Consequently second segment 100B can only operate when plugged into (i.e., conductively connected to) first segment 100A, which is connected to the frequency controller 104 and in the depicted example includes a feedback sensor assembly 114. In implementations in which other segments 100 are present between the first segment 100A and second segment 100B, these segments will also not be independent as their operation will depend on being connected to the first segment 100A (and being thereby connected to the frequency controller 104 and/or feedback sensor assembly 114) and to the second segment 100B (and being thereby connected to the motor termination connections 110).

As noted immediately above, in the depicted example one of the stator segments 100 (here first segment 100A) contains a feedback sensor assembly 114, such as a Hall effect sensor assembly. This feedback sensor assembly 114 is used in the depicted brushless DC servo motor 90 to provide commutation feedback to the frequency controller (i.e., servo drive) 104. Alternatively, in other implementations, a wide bore encoder or other comparable approach may be employed to provide feedback to the frequency controller 104. In the depicted example, the feedback sensor assembly 114 is located in the first segment 100A, which is connected to the frequency controller 104. Such an arrangement may offer benefits in terms of electrical noise and/or signal degradation as the feedback sensor assembly 114 and frequency controller 104 are closer (in terms of electrical path length), thus minimizing or reducing the potential for electrical noise and/or signal degradation between the feedback sensor assembly 114 and the frequency controller 104.

Figure 3:
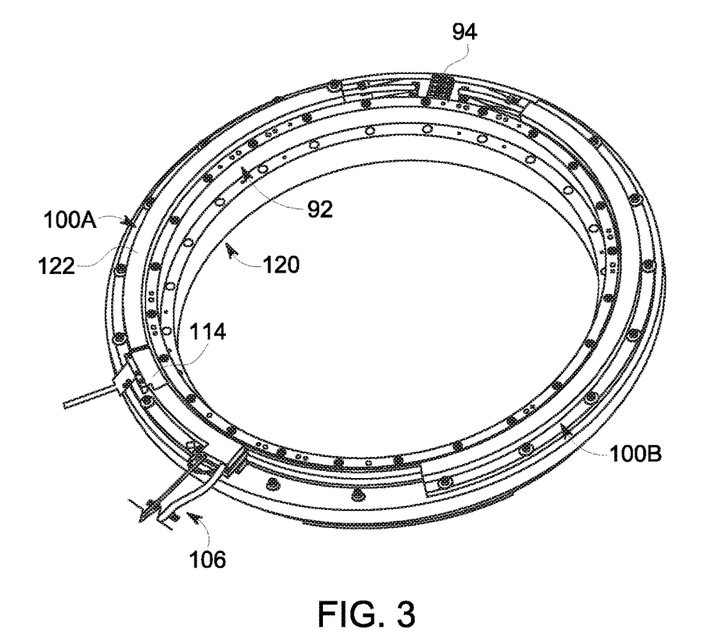
FIG. 3 depicts a three-dimensional design view of the motor assembly of FIG. 2 in conjunction with a bearing assembly, in accordance with aspects of the present disclosure.

Turning to FIG. 3, a perspective design-type view based on the general assembly of FIG. 2 is shown. In the example of FIG. 3, the motor rotor 92 and motor stator 98 are shown mounted to a bearing rotor/stator assembly 120 (discussed in greater detail below). For example, as discussed below, the motor stator 98 may be bolted or otherwise affixed to a bearing stator of the bearing assembly 120 while the motor rotor 92 is bolted or otherwise permanently connected to a bearing rotor of the bearing assembly 120. In addition a potting material 122, such as a thermally conductive potting material, is shown encapsulating or coating the armature windings of the stator segments 100A, 100B. The potting material 122 may be provided so as to protect the stator armatures from damage (such as shipping vibration or handling damage) and to provide a heat dissipation interface during operation.

As can be seen in FIG. 3, the stator segments 100A, 100B are fully supported by (i.e., connected to) the bearing assembly 120 over their full length. Such complete contact or support helps to reduce or eliminate structural vibration from the armature winding during operation. Further, the complete contact formed between each stator segment 100 and the connected bearing assembly provides a thermal heat transfer path from the windings of the stator into the bearing housing, which in turn is connected to the stationary gantry structure. This thermal heat transfer path helps to conduct heat into the bearing assembly and connected structures, providing improved cooling.

Figure 4:
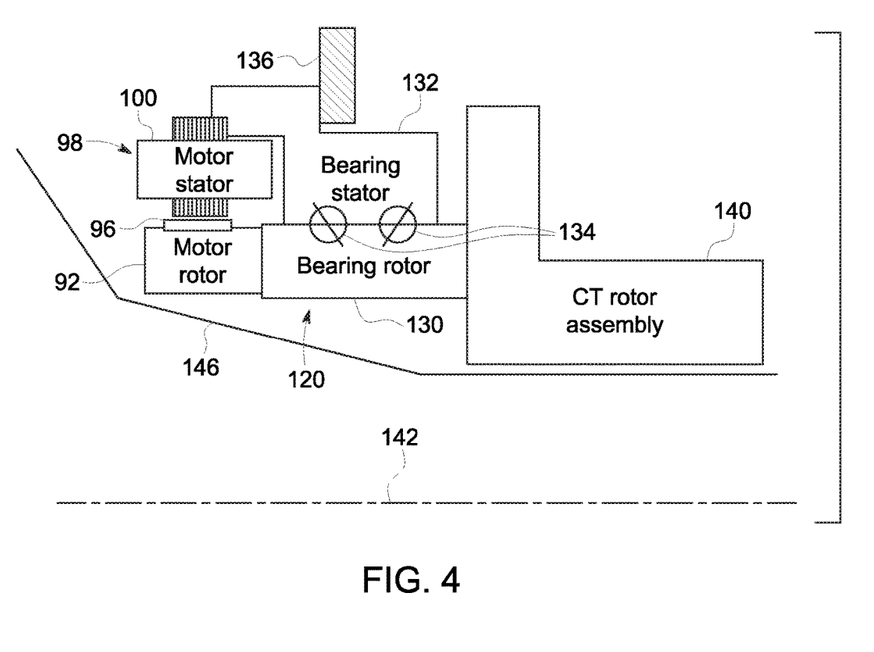
FIG. 4 is a cross-section view taken through the bearing assembly and motor assembly of FIG. 3, in accordance with aspects of the present disclosure.

FIG. 4 is a cross-section view taken through a segmented stator of a motor assembly and the associated bearing assembly, as shown in the preceding example. In this example, the engagement between the motor assembly (i.e., motor stator 98 and motor rotor 92) and the bearing assembly 120 (i.e., bearing rotor 130 and bearing stator 132, rotatably engaged by bearings 134) can more clearly be seen. In particular, the motor stator 98 (composed of stator segments 100 as discussed herein) is coupled (e.g., bolted) to the bearing stator 132, which in turn is coupled (e.g., bolted) to a fixed and stationary component 136 of the imaging system 10, such as a structural frame of the system 10, which is relatively fixed and immobile (i.e., stationary). Thus, by this coupling the bearing stator 132 and securely coupled motor stator 98 (formed from the separate stator segments 100) are securely held stationary.

Conversely, the rotating components (i.e., motor rotor 92, bearing rotor 130, and CT rotor assembly 140) may rotate with respect to these stationary components about a rotation axis 142 of the system 10 (typically running through the bore of the gantry 12) during operation. In particular, the CT rotor assembly 140 may serve as an attachment for the rotating scanner elements of the system 10, such as source 14 and detector 20. The CT rotor assembly 140 is in turn affixed (e.g., bolted) to the bearing rotor 130 which rotates with respect to the stationary bearing stator by means of the bearings 134 allowing rotational motion between the bearing stator 132 and bearing rotor 134. The bearing rotor 130 is affixed (e.g., bolted) to the motor rotor 92, which as shown above, is formed as a ring structure having permanent magnets 96 placed on the outer circumference of the ring.

Motive force is provided by the electromagnetic interaction of the motor stator 98 (in the form of stator segments 100) with the permanent magnetic field provided by magnets 96 on the motor rotor 92. In particular, the stator segments 100 include armature windings (i.e., conductive wire or coil windings) through which a current is passed to generate a magnetic field, which in turn induces rotational movement of the motor rotor 92 within the ring of the motor stator 100 via interaction with the permanent magnetic field of the rotor 92. The fixed attachment of the motor rotor 92 to the rotatable bearing rotor 130 of bearing assembly 120 causes rotation of the bearing rotor 130 relative to the bearing stator 132, and corresponding rotation of the rotor assembly 140 relative to the stationary structure 136. In practice, a stationary cover or housing 146 may also be provided over the motor and bearing components so as to separate the mechanical components from the patient environment. In practice, the rings formed by the motor rotor 92, bearing rotor 130, and rotor assembly 140 are sized so that their inner diameters accommodate a patient passing through these components for imaging.

Figure 5:
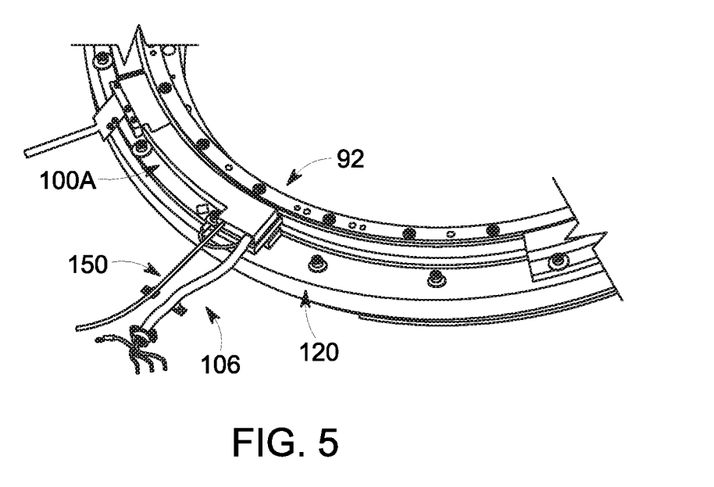
FIG. 5 depicts a view of the connection formed between adjacent stator segments, in accordance with aspects of the present disclosure.
Figure 6:
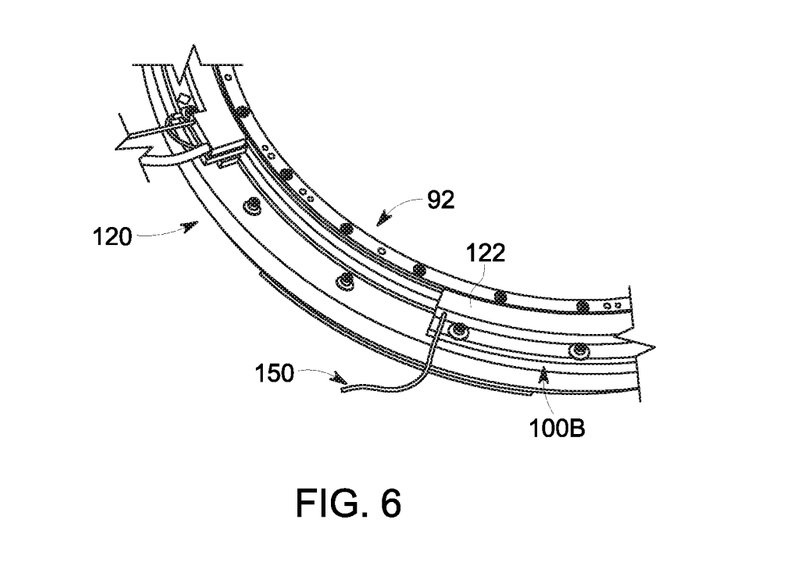
FIG. 6 depicts a view of the connection end of a first stator segment, showing, in accordance with aspects of the present disclosure.
Figure 7:
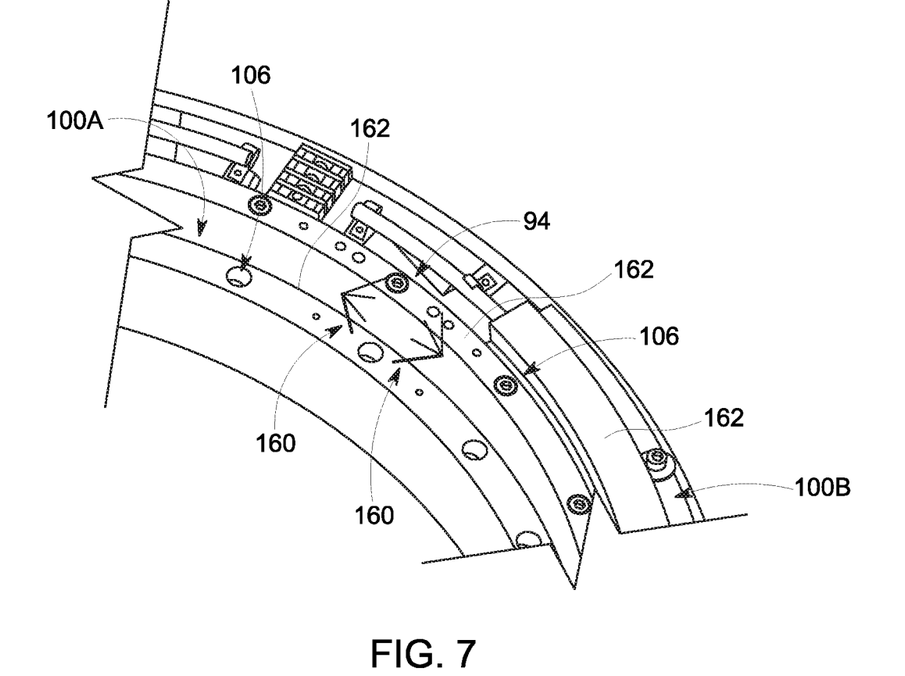
FIG. 7 depicts a view of the terminal end of a terminal stator segment, showing, in accordance with aspects of the present disclosure.

With the preceding in mind, FIGS. 5-7 depict a variety of close-up views of certain features that may be present in a motor assembly as described herein. For example, FIGS. 5 and 6 each depict the use of thermal sensors connected via cabling 150 with the various stator segments 100A (FIG. 5) and 100B (FIG. 6). In FIG. 5, the thermal sensors, via cable 150, monitor (periodically or on demand) a temperature of the armature winding of the stator segment 100A, which may be used in controlling operation of the direct drive motor employing the stator segments. FIG. 5 also depicts in greater detail the motor cable 106 and its connection to the first stator segment 100A.

Similarly, in FIG. 6, the thermal sensors, via cable 150, monitor (periodically or on demand) a winding temperature of the stator segment 100B which may also be used in controlling operation of the direct drive motor employing the stator segments. FIG. 6 also depicts in greater detail the motor winding end termination, typically located beneath the potting encapsulation 122.

Turning to FIG. 7, the terminal block 94 or other connection arrangement (e.g., a set of connectors) and interconnection between serially connected stator segments 100A and 100B is shown in greater detail. In the depicted example, motor cables 106 are used to connect the stator segments 100A and 100B through terminal block or other connector arrangement 94. The motor cables 106 are short in length and may be shielded (e.g., may include a copper or other suitable shield material or structure) to reduce radiated electrical emissions (EMC) by the motor wires 160 contained within the cables 106. Near the terminal block 94 (or equivalent connector structure), the motor wires 160 may emerge from motor cables 106 to be connected at the terminal block 94. In the depicted implementation, the motor cables 106 between the stator segments 100 and terminal block 94 are clamped (e.g., using clamps 162) so as to ground the shielded cables 106. In other implementations, other suitable mechanisms may be employed for grounding the cables 106 at each end.

While the preceding generally relates the use, and benefit, of a fully segmented stator assembly, it should also be appreciated that other configurations may also be possible. For example, instead of full segmentation (i.e., separable stator structures), it may instead be possible to utilize a partial-segmented motor assembly, in which the stator motor ring is instead formed as a full round stator lamination stack, but in which the windings are only wound in certain distinct and separate sections consistent with the fully segmented stator and windings discussed herein. Such a configuration would reduce the torque on the motor, as would the fully segmented configurations discussed herein, but would not achieve the cost reduction of the fully segmented designs due to the reliance on a full ring of lamination stacks. The partial segmented approach would reduce the weight of the stator assembly, but not as much as a fully segmented design, and the electrical radiated emissions would be similar to what would be achieved using a fully segmented motor stator as discussed herein as the wound areas of the stator would be connected in series to on another.

Technical effects of the invention include a direct drive motor for use in a CT gantry having a segmented motor stator assembly. The stator segments are connected in series, allowing short cables to be used for all connections to minimize electrical emissions. The stator segments are not independently operable and are instead connected in series to, and operated by, a single frequency controller.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A motor assembly for directly driving a gantry of a computed tomography (CT) imaging system, comprising:
    a motor stator comprising two or more separate stator segments electrically connected in series to form a partial ring;
    a motor rotor configured as a ring and positioned within the partial ring of the motor stator; and
    a frequency controller connected to a stator segment of the two or more separate stator segments.

2. The motor assembly of claim 1, further comprising:
    a bearing assembly, comprising:
        a bearing stator affixed to each separate stator segment;
        a bearing rotor affixed to the motor rotor; and
        a plurality of bearings disposed between the bearing rotor and bearing stator so as to allow rotation of the bearing rotor within the bearing stator.

3. The motor assembly of claim 2, further comprising a stationary component to which the bearing stator is secured.

4. The motor assembly of claim 2, further comprising a CT rotor assembly to which the bearing rotor is affixed and which is configured to rotate as the bearing rotor rotates.

5. The motor assembly of claim 4, where the CT rotor assembly further comprises an X-ray source and X-ray detector positioned on opposite sides of the CT rotor assembly.

6. The motor assembly of claim 1, further comprising a terminal block or connector between each pair of adjacent stator segments, wherein each pair of adjacent stator segments is connected in series via the respective terminal block or connector.

7. The motor assembly of claim 1, further comprising a feedback sensor assembly positioned with respect to at least one of the two or more separate stator segments and configured to provide a feedback signal to the frequency controller.

8. A method of assembling a motor assembly of a direct drive for rotating a computed tomography (CT) gantry, comprising:
    affixing a motor rotor to a bearing rotor rotationally coupled to a bearing stator;
    affixing a plurality of stator segments to the bearing stator so as to form a partial ring along the bearing stator, wherein the plurality of stator segments comprise a first stator segment;
    electrically connecting the plurality of stator segments in series; and
    connecting the first stator segment to a frequency controller.

9. The method of claim 8, further comprising affixing the bearing stator to a stationary component.

10. The method of claim 8, further comprising affixing a CT rotor assembly to the bearing rotor such that the CT rotor assembly rotates when the bearing rotor rotates.

11. The method of claim 10, further comprising positioning an X-ray detector and an X-ray source on opposite sides of the CT rotor assembly.

12. The method of claim 8, wherein electrically connecting the plurality of stator segments in series comprises connecting adjacent stator segments via a respective terminal block or connector.

13. The method of claim 8, further comprising positioning a feedback sensor assembly with respect to a respective stator segment, wherein the feedback sensor assembly provides a feedback signal to the frequency controller.

14. A computed tomography (CT) system, comprising:
    a stationary frame;
    a CT rotor assembly;
    a frequency controller;
    a motor assembly comprising:
        a motor stator formed as a partial ring, wherein the motor stator comprises a plurality of stator segments electrically connected in series, wherein the plurality of stator segments comprise a first stator segment, and wherein the first stator segment is electrically connected to the frequency controller;

a motor rotor positioned within the motor stator and configured to rotate within the motor stator when the frequency controller applies a current to windings of each stator segment; and a bearing assembly connected to the motor assembly, the bearing assembly comprising:
 a bearing rotor affixed to the motor rotor on a first rotor surface and to the CT rotor assembly on a second rotor surface;
 a bearing stator affixed to the motor stator on a first stator surface and to the stationary frame on a second stator surface; and
 a plurality of bearings between the bearing rotor and bearing stator configured to allow rotation of the bearing rotor within the bearing stator when driven by the motor assembly.

15. The CT system of claim 14, wherein the motor rotor comprises a plurality of permanent magnets positioned on an outer circumference of the motor rotor.

16. The CT system of claim 14, further comprising:
 a CT rotor assembly to which the bearing rotor is affixed and which is configured to rotate as the bearing rotor rotates.

17. The CT system of claim 16, wherein the CT rotor assembly further comprises an X-ray source and X-ray detector positioned on opposite sides of the CT rotor assembly.

18. The CT system of claim 14, wherein the motor stator further comprises a terminal block or connector between each pair of adjacent stator segments, wherein each pair of adjacent stator segments is connected in series via the respective terminal block or connector.

19. The CT system of claim 14, further comprising a feedback sensor assembly positioned with respect to a respective stator segment and configured to provide a feedback signal to the frequency controller.

* * * * *